United States Patent [19]

Sahota

[11] Patent Number: 5,320,605
[45] Date of Patent: Jun. 14, 1994

[54] MULTI-WIRE MULTI-BALLOON CATHETER

[76] Inventor: Harvinder Sahota, 3861 Wisteria, Seal Beach, Calif. 90740

[21] Appl. No.: 7,767

[22] Filed: Jan. 22, 1993

[51] Int. Cl.⁵ .......................................... A61M 29/00
[52] U.S. Cl. .................... 604/101; 606/194
[58] Field of Search .............. 604/95, 96, 49–54, 604/101, 264; 606/191–195

[56] References Cited

U.S. PATENT DOCUMENTS

| | | |
|---|---|---|
| 2,930,377 | 3/1960 | Cowley . |
| 3,043,677 | 7/1962 | Wallace . |
| 3,448,739 | 6/1969 | Stark et al. . |
| 3,889,686 | 6/1975 | Duturbure . |
| 4,040,413 | 8/1977 | Ohshiro . |
| 4,233,983 | 11/1980 | Rocco . |
| 4,329,993 | 5/1982 | Lieber et al. . |
| 4,338,930 | 7/1982 | Williams . |
| 4,423,725 | 1/1984 | Baran et al. . |
| 4,461,280 | 7/1984 | Baumgartner . |
| 4,527,549 | 7/1985 | Gabbay . |
| 4,546,759 | 10/1985 | Solar . |
| 4,547,193 | 10/1985 | Rydell . |
| 4,563,181 | 1/1986 | Wijayarathna et al. . |
| 4,581,017 | 4/1986 | Sahota . |
| 4,644,936 | 2/1987 | Schiff . |
| 4,689,040 | 8/1987 | Thompson . |
| 4,738,666 | 4/1988 | Fuqua . |
| 4,762,129 | 8/1988 | Bonzel . |
| 4,763,654 | 8/1988 | Jang . |
| 4,784,639 | 11/1988 | Patel . |
| 4,822,345 | 4/1989 | Danforth . |
| 4,824,435 | 4/1989 | Giesy et al. . |
| 4,826,480 | 5/1989 | Diaz et al. . |
| 4,932,413 | 6/1990 | Shockey et al. . |
| 4,960,411 | 10/1990 | Buchbinder . |
| 4,983,167 | 1/1991 | Sahota . |
| 4,988,356 | 1/1991 | Crittendon et al. . |
| 5,002,531 | 3/1991 | Bonzel . |
| 5,019,042 | 5/1991 | Sahota . |
| 5,071,406 | 12/1991 | Jang . |
| 5,090,958 | 2/1992 | Sahota . |
| 5,092,873 | 3/1992 | Simpson et al. .............. 604/101 X |
| 5,147,377 | 9/1992 | Sahota . |
| 5,163,906 | 11/1992 | Ahmadi ........................ 606/194 X |
| 5,226,889 | 7/1993 | Sheiban ......................... 604/101 |

FOREIGN PATENT DOCUMENTS

| | | |
|---|---|---|
| 214721 | 3/1987 | European Pat. Off. . |
| 344530 | 5/1989 | European Pat. Off. . |
| 8303766 | 11/1983 | World Int. Prop. O. . |
| 8800071 | 1/1988 | World Int. Prop. O. . |

*Primary Examiner*—John D. Yasko
*Attorney, Agent, or Firm*—Knobbe, Martens, Olson & Bear

[57] ABSTRACT

Dilatation catheters for use in administering treatments to relieve stenotic regions within a body lumen are described. In one aspect of the invention, a two wire catheter system, of minimal diameter for treating distal arteries is disclosed. In another aspect of the invention, a multiple wire multiple balloon system in disclosed, in which a first balloon on a first catheter is disposed distally of a second balloon on a second associated catheter. Additional balloons and associated catheters may also be incorporated into the multiple wire multiple balloon system. Methods are also discussed for accomplishing sequential dilatations using a multiple wire multiple balloon catheter.

21 Claims, 8 Drawing Sheets

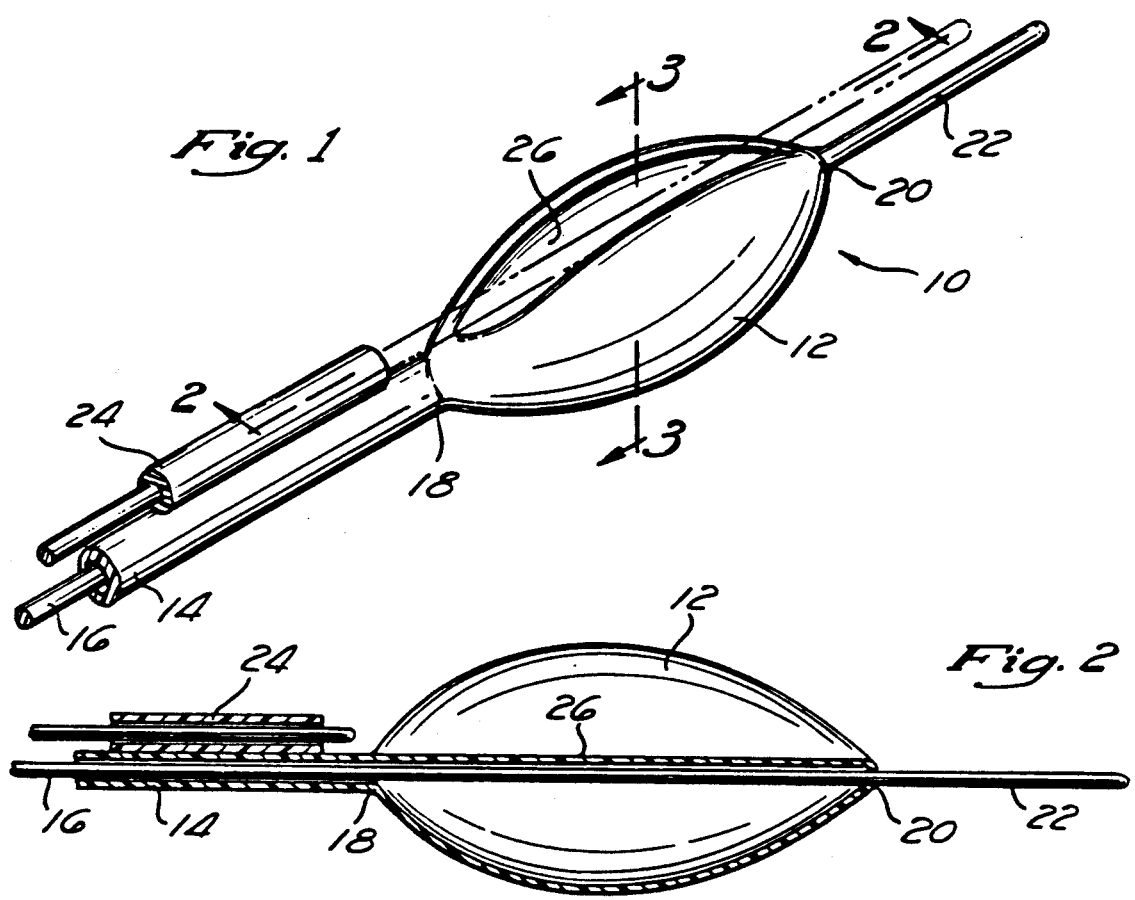
Fig. 1
Fig. 2
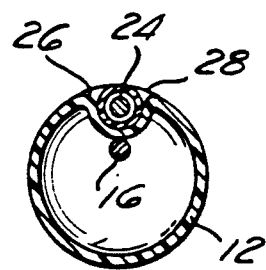 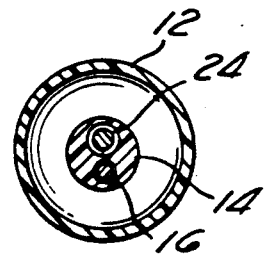 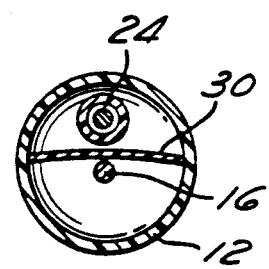
Fig. 3   Fig. 3a   Fig. 3b
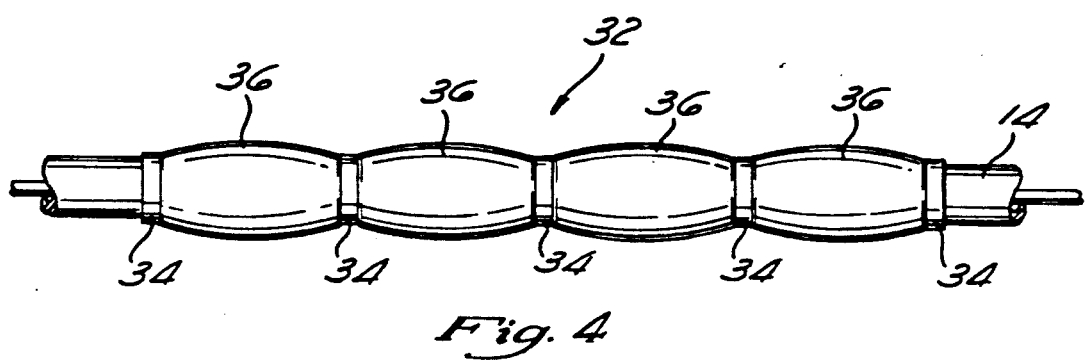
Fig. 4

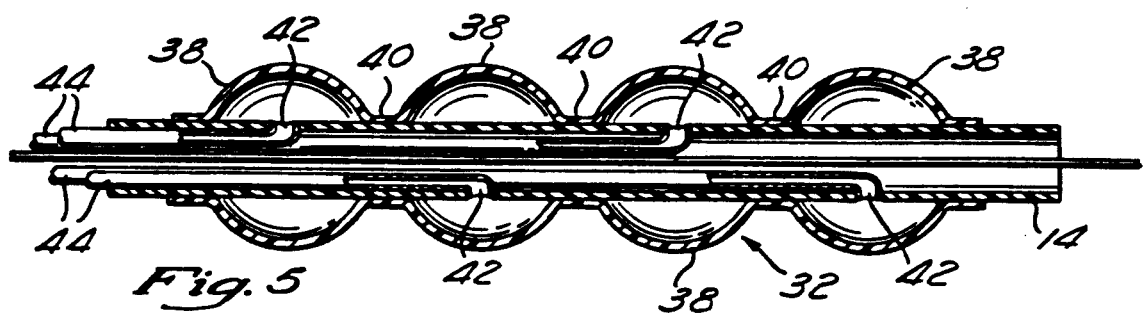
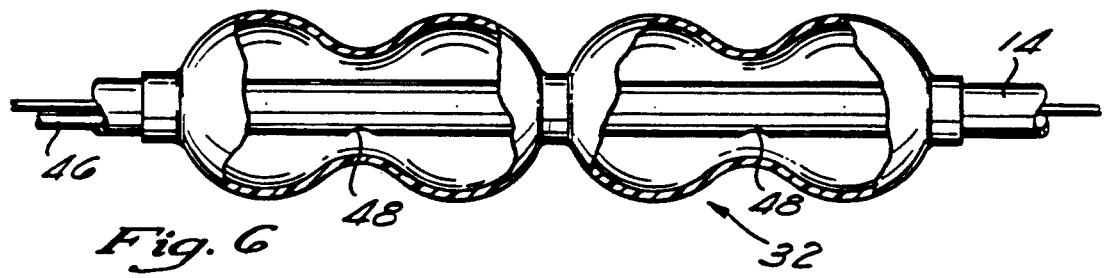
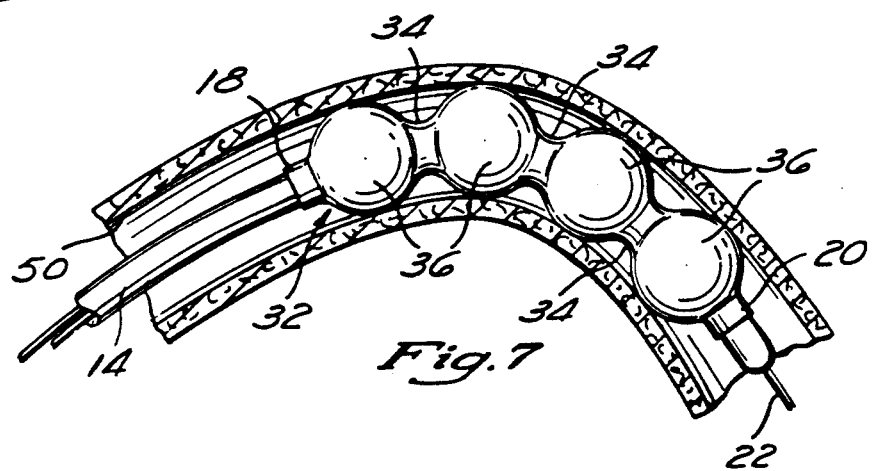
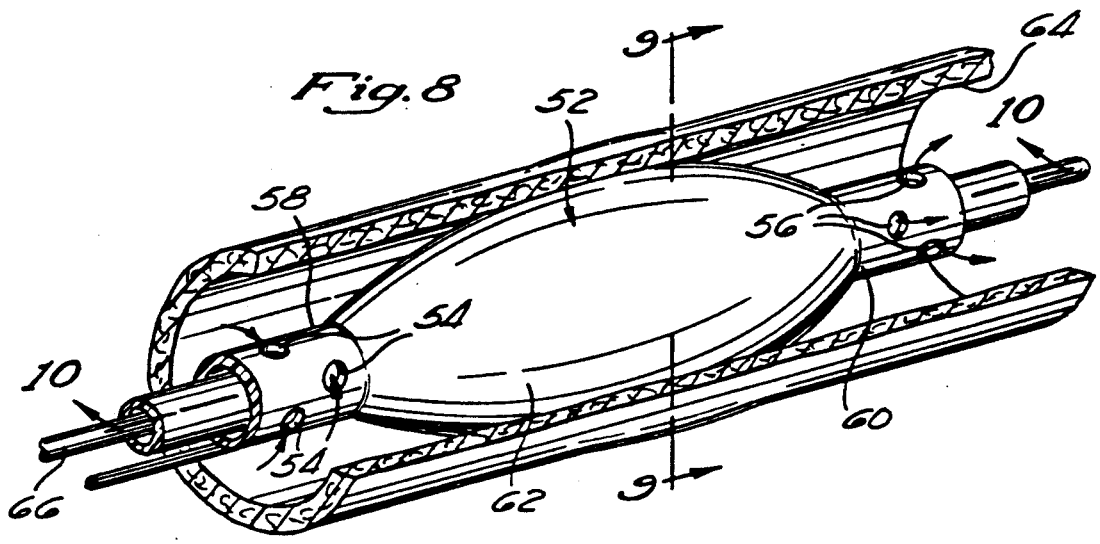

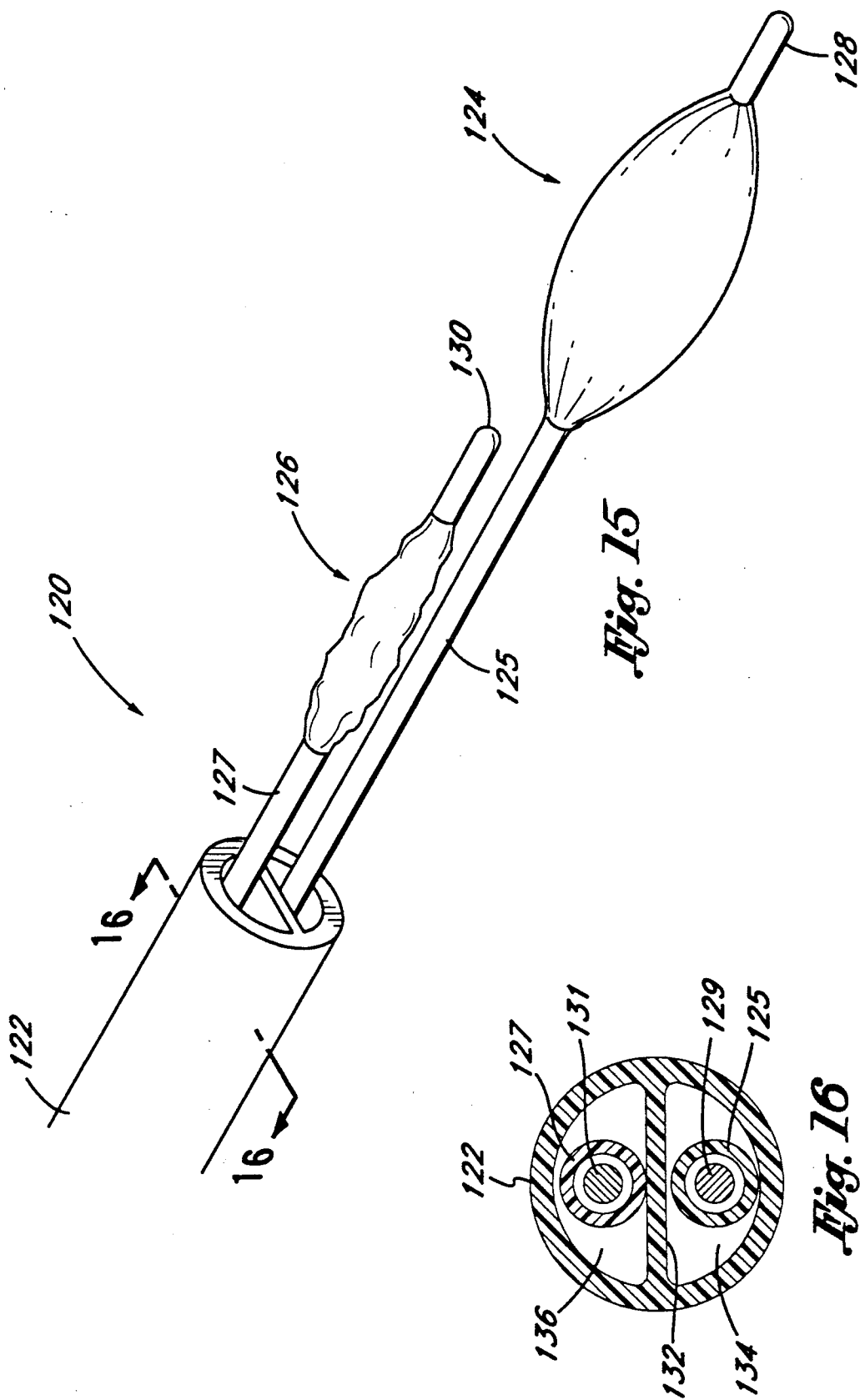

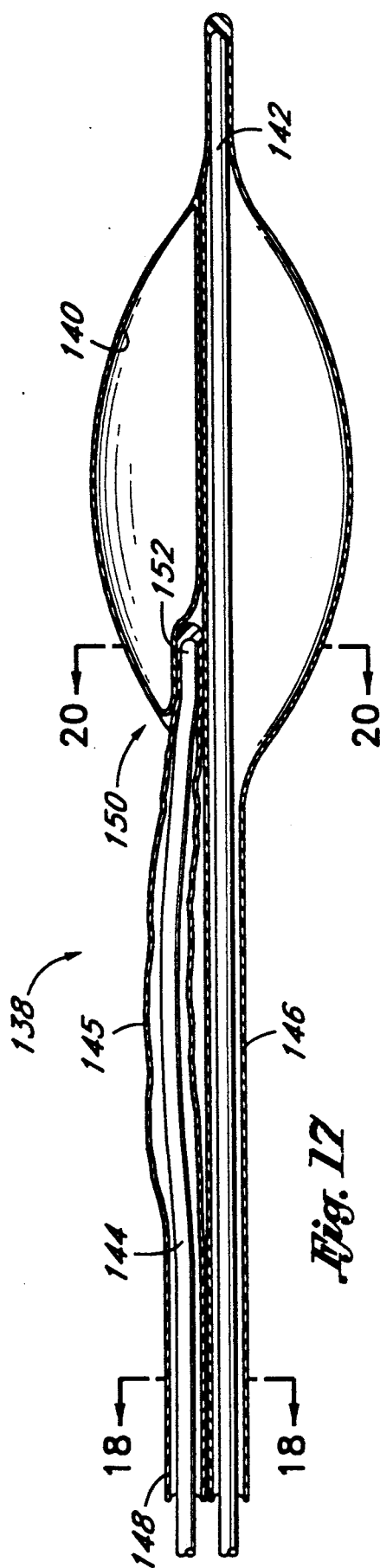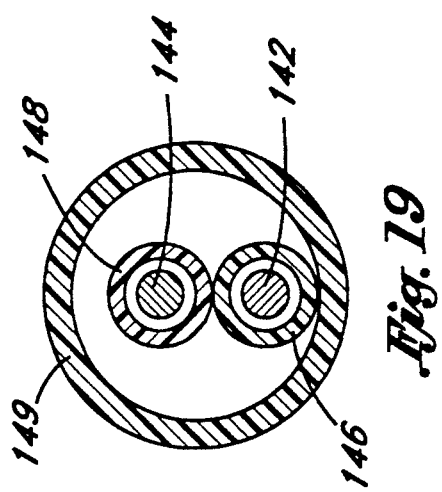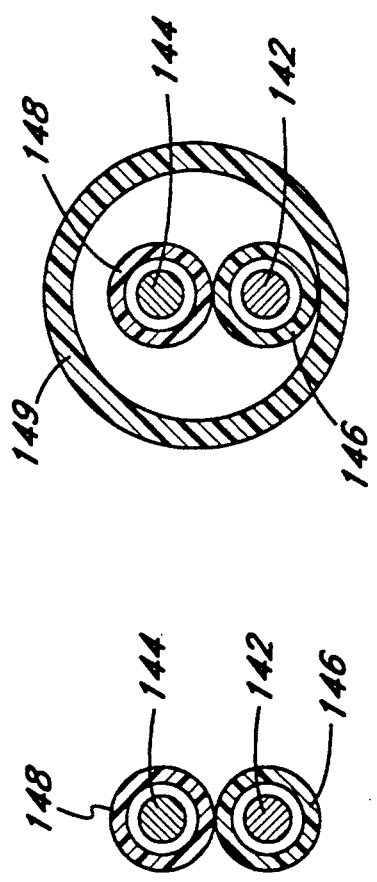

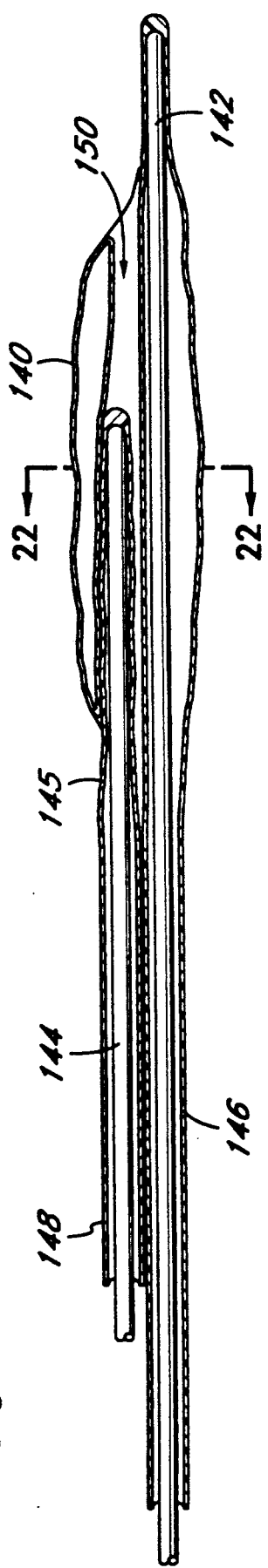
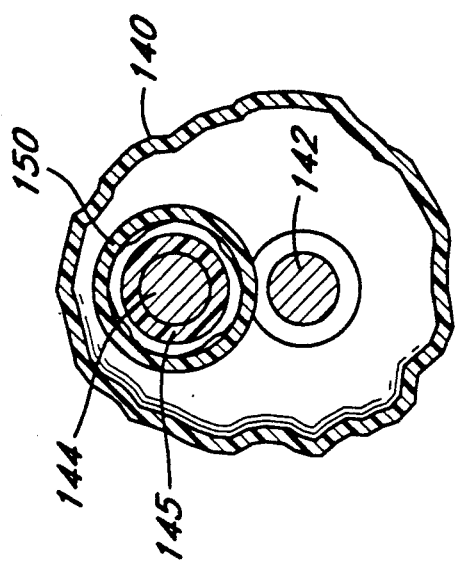
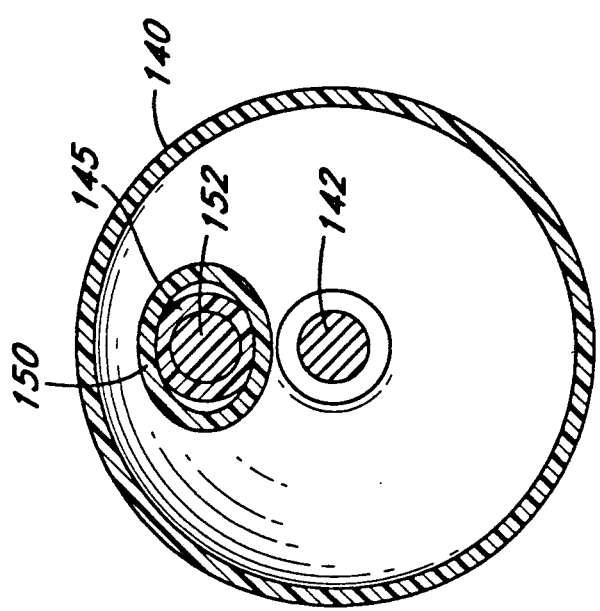

MULTI-WIRE MULTI-BALLOON CATHETER

BACKGROUND OF THE INVENTION

The present invention relates generally to the field of catheters. More specifically, the present invention relates to dilatation catheters for use in administering treatments to relieve a stenotic region or to widen a constricted blood flow or tubular passage, such as the coronary artery, as well as other vessels.

Percutaneous transluminal coronary angioplasty (PTCA), a procedure for treating a patient having a stenosis or constricted blood region in a coronary artery, has become a widely accepted therapeutic alternative to coronary arterial bypass surgery for many patients. PTCA increases the lumen by radial expansion. The main advantage of PTCA rests in the avoidance of the immediate post-operative discomforts associated with coronary bypass surgery, and certainly in the reduction of morbidity by use of this procedure.

The benefits of PTCA are restricted to lesions accessible to the balloon dilatation catheter. With standard systems, certain lesions are inaccessible due to variations in the patient's anatomy and vasculature. Further, seducing side branches, tortuous vessels, and the more distal arteries have presented serious difficulties in the PTCA procedure because, due to its cross-sectional area, the balloon could not reach the stenotic region.

Performing a coronary angioplasty involves the difficulty of inserting a balloon catheter into the desired coronary artery. Most balloon catheters are too flexible for direct insertion into the patient's coronary artery. Accordingly, the standard angioplasty process begins with the insertion of a guiding catheter, or sleeve into the obstructed vessel, under local anesthesia. To facilitate the introduction of the guiding catheter, and to avoid damage to the body lumen at the puncture site, a guide wire may be useful in the insertion of the guiding catheter. The guiding catheter is designed to provide a conduit through which a balloon catheter is not tapered so as to permit the unimpeded passage of the balloon catheter therethrough.

When considering angioplasty as a method of treating stenotic regions, the morphology of the lesion is critical in determining whether the balloon catheter can be safely passed beyond the stenosis, and whether the vessel will adequately dilate. If the stenosis is comprised primarily of fatty deposits, for example, it is often times possible to compress the stenosis radially outwardly, against the adjacent vessel wall, so as to increase the cross-sectional area of the vessel, and provide adequate perfusion through the vessel. If, however, the artery is hard, or the stenosis has calcified, a standard balloon might burst when inflated. Further, tortuous hardened arteries may be dissected if inflated with such a dilatation balloon.

The lesion may be approached with a guide wire by advancing the catheter and guide wire as a unit, or by advancing the guide wire first. Steering the tip of the wire is done by the surgeon or by an assistant. If the tip is moving in an undesired direction, then slight withdrawal and rotation of tip will point it in the correct way. Once the wire is positioned, the balloon catheter may be advanced over it until it crosses the lesion while the surgeon pulls back on the guide wire to maintain the tip in a fixed position in the distal coronary. If resistance is encountered at the lesion, gentle pressure on the balloon catheter will often cause it to cross. If, however, the lesion is too tight or hard and the balloon tip still will not cross, a new, low profile catheter must be selected. In this instance, the safety of the movable guide wire system must be sacrificed.

Ordinarily, a cardiologist, administering an angioplasty treatment, does not know how much pressure to apply to the balloon to achieve satisfactory results. Since the balloon is non-distensible, it can be inflated only to the constructed size of the balloon. Further attempts to force fluid into the balloon will result in increased pressure, but no significant increase in diameter. However, excessive pressure in the balloon may dissect the artery, which may cause serious damage to the patient's heart.

Therefore, the cardiologist positions the balloon in the artery, expands the balloon, and then allows the balloon to depressurize to permit measurement of blood flow across the stenosis. If the blood flow rate is not acceptable, the cardiologist must repeat the angioplasty treatment, often times necessitating the insertion of multiple catheters, of progressively larger diameters, to gradually increase the lumen of the artery until the obstruction is either alleviated, or until the cardiologist determines that angioplasty will be unable to restore the blood flow rate to an acceptable value.

When the angioplasty procedure requires the insertion and withdrawal of a great many balloon catheters, the risk of damage to the lining of the blood vessel is substantially increased. All blood vessels have a lining of very flattened cells, known as endothelial cells, the integrity of which is essential to normal blood flow. Damage or injury to the endothelial layer promotes the adherence of blood cells passing through the vessel at the point of injury, and may form further obstructions within the artery or vessel.

SUMMARY OF THE INVENTION

The dilatation catheters of the present invention overcome many of the difficulties associated with ordinary prior art dilatation catheters. In one aspect of the invention, a two wire system, of minimal diameter is disclosed. In this embodiment, the dilatation balloon is secured directly to an advance wire and a second movable wire is provided. Advantageously, following inflation and deflation of the dilatation balloon, the catheter is withdrawn across the lesion while the second, movable wire is advanced, so as to keep it far distal to the dilated segment. Significantly, if the results are unsatisfactory, or if dissection or other filling defects obscure the lesion, the same dilatation balloon, or a different size or type of dilatation balloon can be quickly and safely passed across the stenosis over the second wire which has been left in place. In addition to providing distal access to the dilated segment, the movable wire gives strength and support along the length of the catheter during insertion thereof, while maintaining the smallest possible profile at the distal end of the catheter to facilitate the ease of insertion past the stenotic region. The added strength and support of the catheter is helpful in manipulating the catheter through the desired vessels.

In accordance with a further aspect of the present invention, there is disclosed a multiple wire multiple balloon catheter for treating a site within a body lumen. The catheter comprises a first elongate flexible wire, and a first dilatation balloon on the first wire. The first dilatation balloon has at least one lumen extending at least part way through the balloon from the proximal edge thereof towards the distal edge thereof.

A second elongate flexible wire is also provided on the catheter, together with a second dilatation balloon on the second wire. The second wire has a distally extending advance wire on the distal side of the second balloon, and at least a portion of the advance wire extends within the proximal opening of the lumen on the first balloon.

Preferably, a lumen extends at least part way into the second balloon from the proximal end thereof towards the distal end thereof, to accommodate the distal advance wire on the distal end of a third balloon catheter.

In one variation of the present invention, the lumen extends all the way through the first dilatation balloon, so that the second elongate flexible wire and second dilatation balloon can be distally axially advanced through the first balloon.

In accordance with a further aspect of the present invention, there is provided a method of exchanging two or more balloons within a site in a body lumen. The method comprises the steps of providing a multiple wire multiple balloon catheter of the type having a first balloon secured to a first flexible wire and a second balloon secured to a second flexible wire, said first balloon having an axially extending lumen therethrough. The first balloon is positioned within a preselected body site, and inflated to dilate or otherwise treat that site. Thereafter, the second balloon is advanced axially in the distal direction through the lumen in the first balloon, and the second balloon is thereafter dilated to treat a site within the body lumen.

Preferably, the first balloon is deflated prior to the step of advancing the second balloon axially therethrough. Thereafter, the first balloon may be withdrawn in a proximal direction to a site within the body lumen, or entirely away from the patient's body. Alternatively, as desired, the two or more balloons can be inflated simultaneously, either in a side by side or an end to end configuration.

In accordance with a further aspect of the present invention, there is provided a balloon catheter for releasably engaging at least one other balloon catheter for insertion into a body lumen as a single unit, but which single unit is capable of sequential dilatation of a preselected site by two or more distinct balloons. The catheter comprises an elongate flexible catheter comprising a wire, and an inflatable balloon on the wire. The inflatable balloon is in fluid communication with at least one inflation lumen extending axially along the wire.

An engagement structure is provided on the catheter, for engaging the distal tip of a second balloon catheter of the type having an elongate flexible wire and at least one inflatable balloon thereon. The engagement structure is optionally on the elongate flexible catheter shaft, or on the first inflatable balloon.

In a preferred embodiment, the engagement structure comprises an opening on the proximal end of the first dilatation balloon. Preferably, the opening is in communication with a lumen extending axially throughout the length of the first balloon.

Further objects, features and other advantages of the present invention will become apparent from the ensuing detailed description, when considered together with the appended drawings and claims.

BRIEF DESCRIPTION OF THE DRAWINGS

FIG. 1 is a perspective view of a dilatation catheter;

FIG. 2 is a cross-sectional view, taken along line 2—2 of FIG. 1, showing the positioning of a second wire with respect to the dilatation balloon, prior to insertion into a body lumen;

FIG. 3 is a cross-sectional view, taken along line 3—3 of FIG. 1, illustrating one possible arrangement of the second movable wire;

FIG. 3a is a cross-sectional view of an alternative method of securing the second wire to the balloon dilatation catheter of FIG. 1;

FIG. 3b is a cross-sectional view of a second alternative method of securing the second wire to the balloon dilatation catheter of FIG. 1;

FIG. 4 is a perspective view of a multi-lobed dilatation balloon;

FIG. 5 is a cross-sectional view of the multi-lobed dilatation balloon of FIG. 4, illustrating separate inflation lumen and ports for each lobe of the balloon;

FIG. 6 is a cross-sectional view of a variation of the multi-lobed balloon of FIG. 4, illustrating the combination of two lobes inflated by a single inflation lumen and port;

FIG. 7 is a partial cross-sectional view illustrating the dilatation balloon of FIG. 4 positioned within a patient's artery with the lobes inflated;

FIG. 8 is a partial cross-sectional view of a dilatation catheter within a patient's artery, having a plurality of perfusion ports for allowing the continuous passage of blood flow through the artery while the balloon is inflated;

FIG. 15 is a partial perspective view of a multi-wire multi-balloon embodiment of the present invention.

FIG. 16 is a cross-sectional view along the lines 16, 16 in FIG. 15.

FIG. 17 is a side elevational view of a second embodiment of a multi-wire multi-balloon catheter in accordance with the present invention.

FIG. 18 is a cross-sectional view taken along the lines 18, 18 in FIG. 17.

FIG. 19 is a cross-sectional view of an alternate embodiment of the catheter of FIG. 17, including an outer tubular sheath.

FIG. 20 is a cross-sectional view taken along the lines 20, 20 in FIG. 17.

FIG. 21 is a side elevational view of the catheter of FIG. 17, with the distal balloon deflated and the proximal balloon advanced part-way through the distal balloon.

FIG. 22 is a cross-sectional view taken along the lines 22, 22 in FIG. 21.

DETAILED DESCRIPTION OF THE PREFERRED EMBODIMENT

Figure 9:
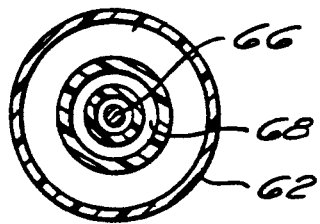
FIG. 9 is a cross-sectional view, taken along line 9—9 of FIG. 8, illustrating the several lumen within the catheter.

Referring now to the drawings in detail, wherein like reference numerals designate like elements throughout the several views thereof, there is shown generally at 10, in FIGS. 1 and 2, a dilatation catheter embodying the present invention in a preferred form. The catheter 10 comprises a dilatation balloon 12, having a distal end 20 which is fastened around an axially elongate wire 16. By attaching the dilatation balloon 12 directly on the wire 16, the catheter 10 has an exceedingly small cross-sectional area, especially designed for insertion into the most distal arteries which are much narrower than the main coronary artery. Preferably, the dilatation balloon 12 is attached to the wire 16 only at the distal end 20, leaving the wire 16 free to move within the shaft 14. Preferably, the wire 16 extends the length of the catheter 10, and exhibits a small segment, referred to as an advance wire 22, which extends beyond the distal end 20 of the dilatation balloon 12. Advantageously, the advance wire 22 may be of any suitable length, and may be preformed to any desired configuration to facilitate insertion of the catheter 10 and passage through the body lumen.

The proximal end 18 of the dilatation balloon 12 tapers to a diameter which approaches that of the wire 16 to form the shaft 14 of the catheter 10. Thus, the catheter shaft 14 is an extension of the dilatation balloon 12. The catheter shaft 14 provides a path for conducting pressurized fluids into and out of the balloon 12 for selective expansion and deflation thereof. Preferably, the balloon 12 and shaft 14 of the catheter 10 are made of a non-distensible material so that it can only be inflated to expand to the constructed size. Further attempts to inflate such structures result in an increase in pressure, but no significant increase in diameter.

A second wire 24 is movably secured to the catheter shaft 14. As illustrated in FIGS. 1 and 3, the second wire 24 may be external to the catheter shaft 14 and held in place by a thin membrane (not shown). The membrane can cover the entire second wire, or can be disposed at intervals along the length thereof. If the second wire 24 is external to the catheter shaft 14, as illustrated in FIGS. 1-3, the dilatation balloon 12 may exhibit a groove 26 on an outer surface thereof, closed off by a thin membrane 28. The membrane covered groove 26 provides a path through which the second wire 24 may slide. Alternatively, the second wire 24 may be movably retained within the catheter shaft 14 in side by side fashion with the first wire 16, as illustrated in FIG. 3a, or within the catheter shaft 14 but separated from the first wire 16 by a partition 30, as illustrated in FIG. 3b. Preferably, the second wire 24 trails the proximal shoulder 18 of the balloon 12 during insertion of the dilatation catheter 10.

The dilatation catheter 10 illustrated in FIGS. 1–3b is particularly suited for use in distal arteries or severe stenosis. In use, the catheter 10 is inserted into the body lumen until the dilatation balloon 12 is proximate the stenotic area. Preferably, the second wire 24 remains behind the balloon portion of the catheter during the initial insertion across the stenotic region so as to maintain the smallest diameter possible when crossing the lesion. Following several inflations and deflations, the balloon 12 is withdrawn across the lesion while the second wire 24 is advanced beyond the dilated segment. The second wire 24 is left in place in the body lumen for a short period of time, referred to as the post-dilatation observation period, which is usually on the order of 15 minutes to ensure that the lumen will not collapse. If occlusion occurs with the wire 24 still in place across the lesion, then there is access to the distal artery, and the same balloon catheter 10, or a different balloon catheter (not shown), can easily be passed across the lesion and the vessel redilated. Thus, once the wire 24 is in place, the surgeon may pass a larger or smaller balloon catheter over the wire to redilate the body lumen. Likewise, this invention offers the surgeon the option of withdrawing the original balloon catheter and directing over the guide wire 24 a catheter having a different balloon configuration or other medical appliance without the difficulty and time require to once again insert the catheter through the body lumen. In this way, if the result is unsatisfactory, or if dissection or other filling defects obscure the lesion, a balloon catheter can be quickly and safely passed across the lesion over the second wire 24 which has been left in place. This is particularly significant in dealing with the more distal arteries, to which access is often times difficult, in that reinsertion of a fresh catheter may not only prove difficult, but also damaging to the endothelial layer and, in emergency situations, too time consuming, dictating the need for emergency bypass surgery, rather than a second attempt at dilatation.

Figure 12:
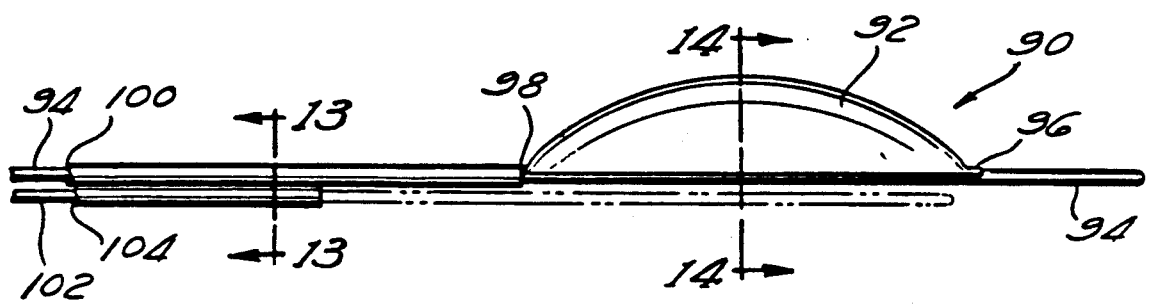
FIG. 12 is a perspective view of a dilatation catheter having a one-sided dilatation balloon, secured to a catheter wire.
Figure 13:
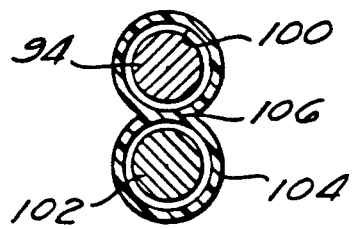
FIG. 13 is a cross-sectional view, taken along line 13—13 of FIG. 12, illustrating the attachment of the one-sided balloon to the catheter wire and the provision of a second, movable wire.
Figure 14:
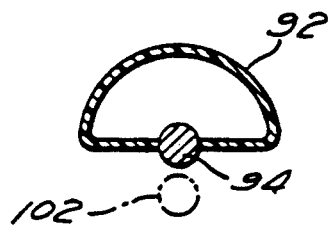
FIG. 14 is a cross-sectional view, taken along line 14—14 of FIG. 12, illustrating the attachment of the dilatation balloon to the catheter wire and, in dotted lines, the positioning of the second wire with respect to the dilatation catheter when advanced.

FIGS. 12–14 illustrate yet an even lower profile dilatation catheter 90. As illustrated, the dilatation balloon 92 of the catheter 90 is a one-sided balloon. The one-sided, or half-circle configuration of the dilatation balloon 92 yields a smaller distal diameter than a balloon which completely encircles the wire 94. Like the catheter 10 illustrated in FIGS. 1-3, the distal end 96 of the one-sided dilatation balloon 82 is secured directly to the wire 94. The proximal end 98 of the balloon 92 tapers and extends longitudinally along the length of the wire 94 to form an inflation lumen 100. A second, movable wire 102 is retained proximate the catheter 90 by a thin hollow membrane 104, secured to the wire 94 which terminates proximate to the proximal end 98 of the dilatation balloon 92. This catheter 90 is particularly useful in dilating severe stenotic regions, where the passage through the artery is very small. In such an instance, the low profile catheter 90 is inserted into the stenosis and inflated to widen the passageway. The dilatation balloon 92 is the deflated, and the movable wire 102 advanced beyond the stenosis so that a second, larger dilatation may be inserted over the wire 92 to adequately dilate the vessel.

Figure 13A:
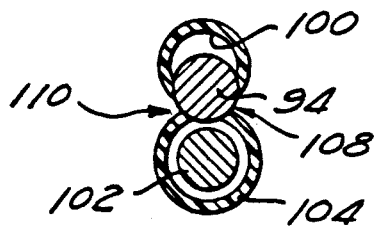
FIG. 13a is a cross-sectional view of an alternative method of securing the second wire to the balloon dilatation catheter of FIG. 12.

As illustrated in FIG. 13, both the hollow membrane 104 and the inflation lumen 100 will form complete circles around the exterior of the movable wire 102 and the catheter wire 94, respectively. The membrane 104 inflation lumen 100 are then secured together so as to share a common outer wall 106. Alternatively, as illustrated in FIG. 13a, the inflation lumen 100 may be wrapped half way around the catheter wire 94 and secured on opposing sides 108, 110 thereof so that the catheter wire 94 forms a portion of the inflation lumen 100. Likewise, the hollow membrane 104 may be wrapped half way around the catheter wire 94 to provide a path through which the movable wire may travel. In the embodiment illustrated in FIG. 13a, the catheter wire 94 provides a common wall for both the inflation lumen 100 and the hollow membrane 104, and thereby yields a smaller diameter catheter shaft.

FIGS. 4–7 are illustrative of a multi-lobed dilatation balloon 32. The multi-lobed balloon 32 is useful in negotiating tortuous vessels and is particularly useful when dilating arteries having acute bends. Preferably, the multi-lobed balloon 32 is a continuous balloon having alternating regions of thick 34 and thin 36 balloon material. The thick portions 34 do not expand as readily as the thin portions 36, and thus the dilatation balloon 32 exhibits multiple lobes, having areas corresponding to the thin portions 36 which readily expand to dilate stenotic areas, and areas corresponding to the thick portions 34 which are resistant to expansion, so as not to straighten arterial bends while the lumen is being dilated. The catheter shaft 14 may be straight, as shown in FIGS. 5 and 6, or it may be preformed with different shapes and configurations to facilitate insertion through the body lumen.

Alternatively, the multi-lobed dilatation balloon 32 may be comprised of a plurality of balloons 38, having overlapping shoulders 40, secured to the exterior of the catheter shaft 14. In such a case, each lobe 38 is advantageously provided with a separate inflation port 42, as illustrated in FIG. 5. As illustrated in FIG. 5, each inflation port may be connected to a separate inflation lumen 44, so that each lobe 38 of the multi-lobed balloon 32 may be separately inflated. Conversely, as illustrated in FIG. 6, a single inflation lumen 46 having a plurality of inflation ports 48 disposed proximate to a lobe of the multi-lobed balloon, or a combination of lobes, may be utilized to inflate each of the lobes simultaneously.

FIG. 7 illustrates a multi-lobed balloon 32 in an inflated state, within a bending body lumen 50. Significantly, as illustrated, the multi-lobed balloon 32 does not force the artery 50 to straighten as the balloon is inflated, but rather, conforms to the arterial bends, so as to reduce the risk of dissection of the artery. Further, the multi-lobed construction of the balloon 32 significantly increases the ease of insertion through tortuous vessels over a straight, single-lobed balloon, in that the multi-lobed balloon is more flexible.

Figure 10:
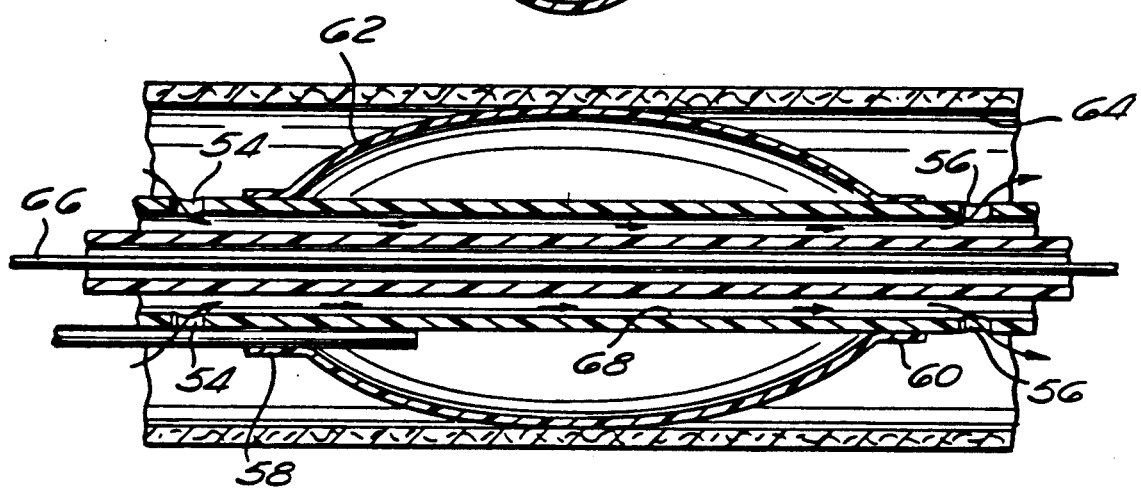
FIG. 10 is a cross-sectional view, taken along line 10—10 of FIG. 8, illustrating, by way of arrows, the perfusion of blood through the inner lumen of the catheter.

FIGS. 8–10 are illustrative of a dilatation balloon catheter 52 having a plurality of perfusion ports 54, 56 on opposite ends 58, 60 of a dilatation balloon 62. As illustrated in FIG. 8, when the balloon 62 is in an inflated state within the artery 64, it completely occludes blood flow past the arterial wall. A bypass lumen 68 which is independent from the lumen through which the guide wire 66 passes, allows blood to perfuse through and bypass the dilation balloon so as to maintain blood flow to the distal side of the occluding balloon. Note that the guide wire need not be withdrawn in order to provide the passage of this blood flow. This is significant in that withdrawal and reinsertion of the guide wire 66 can sometimes result in damage to the arterial walls. Thus, by providing a bypass lumen 68, the dilatation catheter 52 is made safer for the patient.

Not infrequently, it is determined that angioplasty will be unable to restore the blood flow rate to an acceptable level. In such a case, the patient is prepared for emergency bypass surgery. If the catheter is fully withdrawn from the affected vessel and the vessel becomes totally obstructed, infarction of the area distal to the obstruction will begin to occur. A guide wire left in place across the lesion, will provide a small opening through which a small amount of blood may flow beyond the stenosis, however, this blood flow is not usually sufficient to prevent infarction. Advantageously, however, if the dilatation balloon 52 is left across the stenosis in a deflated state, blood will perfuse through the perfusion ports 54, 56 and the bypass lumen 68 to maintain a steady flow of blood distal to the obstruction. Thus, the catheter 52 can effectively serve as a shunt while preparing the patient for emergency bypass surgery.

Figure 11:
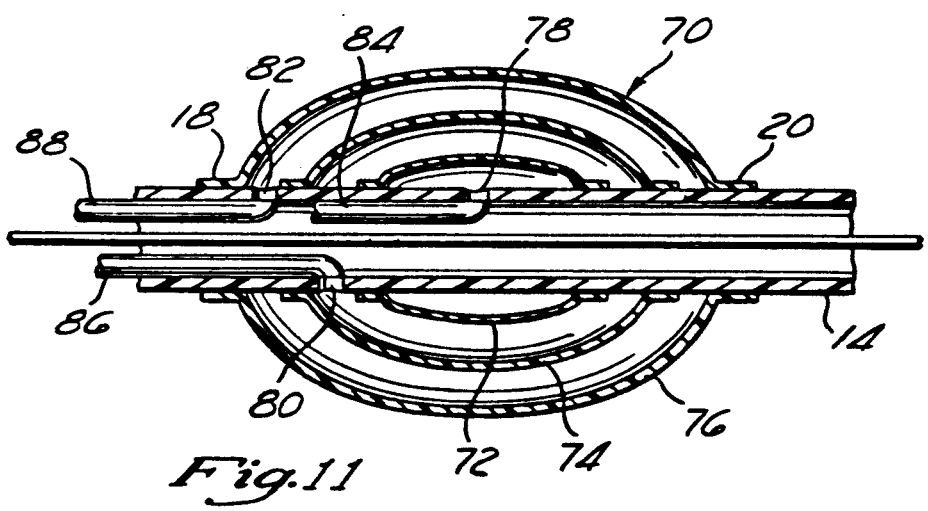
FIG. 11 is a cross-sectional view of a multi-layered dilatation balloon in an inflated state.

In many instances, the body lumen, such as the arteries, veins, and other vessels, tubes, and heart valves are hard, or have calcified fibrous lesions which are resistant to dilatation. Standard angioplasty balloons are often not strong enough to dilate the hardened lesions, and are prone to bursting within the artery necessitating the withdrawal of the catheter and insertion of a new one. Thus, as illustrated in FIG. 11, a dilatation balloon 70, having a plurality of concentric balloon layers 72, 74, 76 is provided. Each balloon layer 72, 74, 76 is provided with a separate inflation port 78, 80, 82 and inflation lumen 84, 86, 88 for selectively inflating the balloon 70. In use, the innermost balloon 72 is inflated first to partially dilate the body lumen. The outer layers 74, 76 of the balloon 70 give additional strength and support to the inner balloon 72 to prevent the inner balloon 72 from bursting. The outer balloons 74, 76 are progressively inflated so as to compress the stenosis radially outwardly, against the adjacent arterial wall. Significantly, the multi-layered balloon 70 of FIG. 11 is also useful in those instances where progressively larger balloons must be used in order to properly dilate the artery or other body lumen or wall of the heart valve.

Referring to FIG. 15, there is disclosed one embodiment of a multi-wire multi-balloon catheter in accordance with the present invention. In general, the multi-wire multi-balloon catheter permits the transluminal placement of more than one balloon on a wire, as a single unit. The balloons can be positioned and inflated sequentially, to accomplish a variety of objectives previously discussed. Alternatively, the two or more balloons can be inflated simultaneously, such as end to end to treat a long lesion or side by side to produce a wider opening. Advantageously, the multi-wire multi-balloon catheters of the present invention exhibit a particularly low profile, and permit the rapid exchange of balloons with minimal trauma to the vascular intima.

Referring to FIG. 15, a multi-wire multi-balloon catheter 120 is illustrated. The catheter comprises generally an elongate flexible tubular housing 122, having at least one axially extending central lumen extending therethrough. A first balloon 124 is secured to a shaft 125 placing the balloon 124 in fluid communication with a proximal source of inflation media. The balloon 124 is further provided with a distal advance wire 128, as has been previously discussed. In FIG. 15, the first balloon 124 is illustrated in an inflated configuration.

A second balloon 126 is illustrated in a deflated configuration. Balloon 126 is secured to an elongate flexible shaft 127 which places the balloon 126 in fluid communication with a proximal source of inflation media. Balloon 126 is similarly provided with an advance wire 130, as has been previously discussed. The second advance wire is preferably provided with an atraumatic tip, such as a rounded end, polymeric bead or other structure known in the art.

The catheter 120 is illustrated in FIG. 15 as it would appear part-way through a multiple balloon dilatation procedure. The first balloon 124 is extended distally of the second balloon 126, and dilated within a preselected site in the body lumen. Following a dilatation in accordance with conventional techniques, the balloon 124 is evacuated. The second balloon 126 is thereafter advanced distally and positioned within the preselected site. Second balloon 126 is thereafter dilated.

The sequential dilatation of two or more balloons can accomplish any of a variety of objectives, as will be understood by one of skill in the art. For example, the balloons can be progressively sized, so that a series of balloons ranging from relatively small to relatively large inflated diameter may be inflated seriatim. Alternatively, the balloons could be of approximately equal size, but utilized to dilate successive axial lengths of a particularly long lesion. Other applications such as treatment of bifurcation lesions and simultaneous dilatations as discussed herein will be apparent to one of skill in the art in view of the present disclosure.

Some additional structural details of the multi-wire multi-balloon catheter of FIG. 15 are revealed in FIG. 16. Referring to FIG. 16, there is disclosed a cross-sectional view of the catheter 120 illustrating the outer tubular housing 122. In this embodiment, two discreet central lumen 134 and 136 are separated by an interior wall 132. The first balloon shaft 125 extends axially through lumen 134. Shaft 125 is spaced radially apart from a central core wire 129, to permit passage of inflation media. Similarly, shaft 127 is radially spaced apart from a central core wire 131 to permit passage of inflation media.

The first balloon shaft 125 and second balloon shaft 127 may be movably associated with one another such as by a tubular sheath 122, as illustrated in FIG. 15, or in any of a variety of other ways previously disclosed for securing the two-wire catheter system. In addition, additional balloons can be readily added to the multi-wire multi-balloon catheters disclosed herein.

Referring to FIGS. 17, 18 and 20, there is disclosed an alternative embodiment of a multi-wire multi-balloon catheter in accordance with the present invention. Catheter 138 generally comprises a first balloon 140 illustrated in an inflated state, and secured to an elongate core wire 142. Wire 142 preferably extends all the way from the first balloon 140 throughout the length of the catheter body to the proximal end thereof.

A second wire 144 is provided with a second balloon 145, illustrated in the deflated condition. As shown in FIG. 17, the second balloon trails the first inflated balloon during insertion and during the initial part of a dilatation procedure.

The first balloon 140 is in fluid communication with an elongate sleeve 146, which is spaced radially outwardly from the core 142 to provide an annular flow path for inflation media, as has been described. Similarly, the second core wire 144 extends axially through an outer sheath 148, which provides fluid communication between the second balloon 145 and a proximal source of inflation media.

The first balloon 140 is provided with a lumen 150 extending axially therethrough. As illustrated in FIG. 17, the distal tip 152 of the second core 144 and balloon 145 extends a small distance into the proximal end of lumen 150. Due to the pressure contained in the inflated balloon 140, the distal portion of the lumen 150 is normally collapsed while the first balloon 140 is in an inflated condition.

Optionally, the second core wire 144 is provided with a slight bowing, as illustrated, or other means to provide a lateral bias in the direction of core wire 142 to help urge the distal tip 152 into the lumen 150.

Referring to FIG. 19, there is disclosed an alternate embodiment of the shaft of the catheter 138, in which each of the elongate tubular bodies 146 and 148 are disposed within an outer tubular sheath 149, similar to sheath 122 in the embodiment illustrated in FIG. 15.

Following evacuation of balloon 140, the collapsing pressure on lumen 150 is relieved and lumen 150 becomes traversable by the second balloon 145. See FIG. 21. After first balloon 140 has been fully evacuated, second balloon 145 is advanced distally with respect to first balloon 140. Relative axial motion of the two balloons can be accomplished manually, by pulling on the proximal end of shaft 146 or pushing on the proximal end of shaft 148. Alternatively, a proximal control having a sliding lever, pistol grip or other convenient structure can be utilized to precisely control an exchange of the positions of the two balloons.

Figure 23:
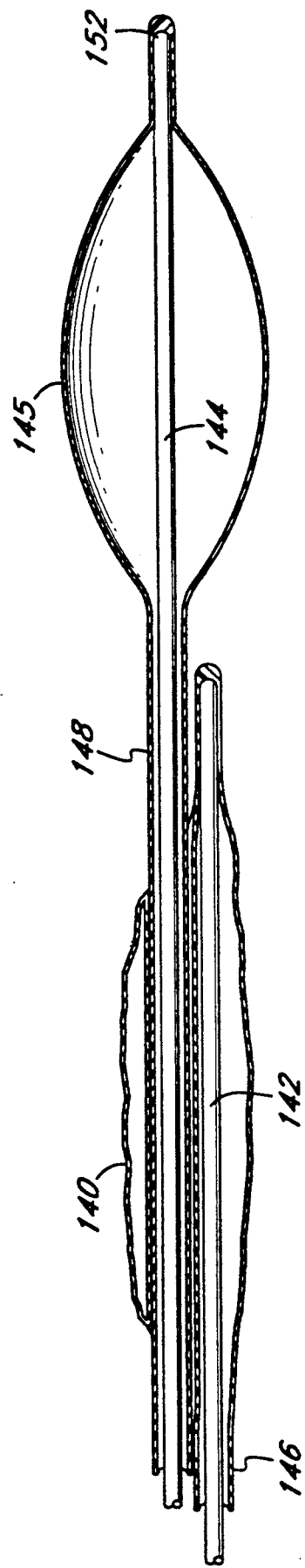
FIG. 23 is a side elevational view of the catheter of FIGS. 17 and 21, illustrating the previously proximal balloon now fully distally advanced and inflated.

Second balloon 145 is eventually extended distally all the way through lumen 150 and beyond first balloon 140, as illustrated in FIG. 23. At that time, second balloon 145 can be inflated within the same or a different treatment site in the body lumen. First balloon 140 and the associated wire 142 and shaft 146 can thereafter be proximally withdrawn, as illustrated in FIG. 23, by proximally sliding along shaft 148. Balloon 140 can be withdrawn part way or all the way out of the patient, to leave only second balloon 145 therein.

In this manner, multiple balloons of exceeding low profile can be rapidly sequentially exchanged without the necessity of removing a balloon proximally along a conventional guide wire and thereafter reinserting and positioning a second or sequential balloon at the treatment site. A third balloon on a wire could be positioned proximally of the first two, and advanced through a second lumen extending through the first balloon 140. Where more than two balloons are desired, the embodiment of the invention illustrated in FIG. 15, without the central wall 132 may be desirable.

Alternatively, third, fourth and further balloons can be sequentially stacked, as in the embodiment of FIG. 17. In this embodiment, the distal advance wire of the third balloon extends into a lumen on the second balloon 145 and the distal advance wire on a fourth balloon extending into a lumen on the third balloon, and so on.

Depending upon the dimensions desired for a particular application, at some point, too many balloons may be sequentially aligned to fit within a lumen extending through the distal most balloon 140. In this event, the wire 142 extending through distal balloon 140 can be given a distal push following deflation of balloon 140. This distal axial travel would free the distal tip 152 of the second balloon 145, and first balloon 140 can thereafter be independently proximally withdrawn from the patient leaving second balloon 145 in the distal-most position. In this embodiment, lumen 150 need not extend throughout the axial length of the balloon. Rather, it need extend only deep enough to capture the distal tip 152 of the next balloon in line. Structures other than a pocket, such as a strap or any of a variety of complementary surface structures, can readily be devised by one of skill in the art.

This design thus permits the use of sequential balloons, while at the same time permitting insertion of the sequential balloons as a single unit, by pre-bending advance wire 142 to steer the catheter in a conventional manner. The overlap of distal tip 152 of the second balloon 145 into the first balloon 140 permits the second balloon and sequential balloons thereafter to track the path of travel which has been created by the first balloon 140.

Thus, there is provided in accordance with the method of the present invention, a method of positioning each of a plurality of balloon on a wire structures, which have been introduced into the body lumen as a single unit. There is also provided a method of sequentially dilating a plurality of balloons within a body lumen, comprising the steps of positioning a first balloon at a preselected site, and dilating the site, thereafter deflating and withdrawing the first balloon. A second balloon is thereafter advanced through the first balloon and dilated at the same or different site. Optionally, a third balloon is advanced distally through the second balloon, and dilated at the same or a different site in the body lumen.

It will be appreciated that certain structural variations may suggest themselves to those skilled in the art. The foregoing detailed description is to be clearly understood as given by way of illustration, the spirit and scope of this invention being limited solely by the appended claims.

What is claimed is:

1. A multiple wire multiple balloon catheter for treating a site within a body lumen, comprising: a first elongate flexible wire;
   a first dilatation balloon on said first wire, said first dilatation balloon having at least one lumen extending at least part way through the balloon from the proximal edge thereof towards the distal edge thereof;
   a second elongate flexible wire; and
   a second dilatation balloon on said second wire, said second wire having a distally extending advance wire on the distal side of said second balloon;
   wherein at least a portion of the advance wire extends within the proximal opening of the lumen on said first balloon.

2. A multiple wire multiple balloon catheter as in claim 1, further comprising a lumen extending at least part way into said second balloon, from the proximal end thereof towards the distal end thereof; and
   a third elongate flexible wire having a third dilatation balloon thereon, said third wire having a distally extending advance wire on the distal side of the third balloon;
   wherein the distal end of the advance wire on the third balloon extends at least part way into the lumen on the proximal end of said second balloon.

3. A multiple wire multiple balloon catheter as in claim 1, wherein said lumen extends axially throughout the entire length of said first dilatation balloon.

4. A multiple wire multiple balloon catheter as in wherein said second balloon has an inflated profile which is different than the inflated profile of the first balloon.

5. A method of exchanging two or more balloons within a site in a body lumen, comprising the steps of:
   providing a multiple wire multiple balloon catheter of the type having a first balloon secured to a first flexible wire and a second balloon secured to a second flexible wire, said first balloon having a lumen extending therethrough;
   positioning said first balloon within a preselected body site;
   inflating said first balloon to dilate said site; and
   thereafter exchanging the relative positions of said first and second balloons by advancing said second balloon axially through the lumen in said first balloon.

6. A method as in claim 5 further comprising the step of deflating said first balloon prior to the step of advancing the second balloon axially therethrough.

7. A method as in claim 5, further comprising the step of withdrawing the first balloon in a proximal direction following evacuation thereof.

8. A method as in claim 5, wherein said exchanging step comprises advancing said second balloon distally.

9. A method as in claim 5, wherein said exchanging step comprises retracting said first balloon proximally.

10. A method as in claim 5, further comprising the step of positioning said second balloon.

11. A method as in claim 10, wherein said positioning step comprises positioning said second balloon at the same site where the first balloon was dilated.

12. A method of sequential dilatation of a preselected site in a body lumen, comprising the steps of:
   introducing a multiple balloon multiple wire catheter into said body lumen, said catheter comprising at least a first dilatation balloon mounted on a first flexible wire and a second dilatation balloon mounted on a second flexible wire, wherein the distal end of the second flexible wire is releasably secured with respect to the first dilatation balloon;
   positioning the first dilatation balloon at a preselected site;
   dilating the first dilatation balloon to radially expand said site;
   deflating said first balloon;
   axially displacing said first balloon in a distal direction with respect to said second balloon thereby disengaging the distal tip of said second wire from said first balloon; and
   thereafter withdrawing said first balloon in a proximal direction.

13. A method as in claim 12, further comprising the step of positioning said second balloon within the body site.

14. A method as in claim 13, further comprising the step of dilating said second balloon.

15. A balloon catheter for releasably engaging at least one other balloon catheter for insertion into a body lumen as a single unit but which is capable of simultaneous or sequential dilatation of a preselected site with two or more distinct balloons; said catheter comprising:
   an elongate flexible wire;
   an inflatable balloon on the wire, in fluid communication with at least one inflation lumen extending axially through the catheter; and
   an engagement structure on the catheter for engaging the distal tip of a second balloon catheter of the type having an elongate flexible wire and at least one inflatable balloon thereon.

16. A balloon catheter as in claim 15, wherein said engagement structure is on the balloon.

17. A balloon catheter as in claim 15, wherein said engagement structure is on the catheter shaft.

18. A catheter as in claim 15, wherein said engagement structure comprises an opening on the proximal end of said first dilatation balloon.

19. A dilatation catheter as in claim 18, wherein said opening is in communication with a lumen extending axially throughout the length of the first balloon.

20. A dilatation catheter as in claim 18, together in combination with a second dilatation catheter of the same structure, wherein the distal tip of said second dilatation catheter is engaged within the opening on the proximal end of said first dilatation balloon.

21. A method of relieving stenotic regions of a body lumen, comprising the steps of:

inserting into said body lumen a first dilation catheter having a first balloon, and an axially elongate first wire, so that only a small advance wire segment extends beyond the distal end of said first balloon, said first balloon having at least one lumen extending axially therethrough;

simultaneously inserting into said body lumen a second catheter having a second balloon, and an axially elongate wire extending through said second catheter, said second dilatation catheter positioned so that said second balloon trails the proximal shoulder of said first balloon during insertion;

injecting a suitable pressurized fluid through said first catheter into said first balloon so as to increase the size of said first balloon;

deflating said first balloon;

withdrawing said first dilatation catheter with respect to said second catheter so that said second balloon is disposed in a relatively distal position; and inflating said second balloon.

\* \* \* \* \*

UNITED STATES PATENT AND TRADEMARK OFFICE
CERTIFICATE OF CORRECTION

PATENT NO. : 5,320,605
DATED : June 14, 1994
INVENTOR(S) : Harvinder M. Sahota

It is certified that error appears in the above-identified patent and that said Letters Patent is hereby corrected as shown below:

Column 11, Line 63, "as in wherein", should be changed to read "as in Claim 1, wherein".

Signed and Sealed this

Sixth Day of June, 2000

Attest:

Q. TODD DICKINSON

Attesting Officer

Director of Patents and Trademarks